United States Patent [19]

Naumann et al.

[11] Patent Number: 4,820,735
[45] Date of Patent: Apr. 11, 1989

[54] VINYLCYCLOPROPANECARBOXYLIC ACID ESTERS

[75] Inventors: Klaus Naumann, Leverkusen; Rudolf Braden, Odenthal; Wolfgang Behrenz, Overath; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 87,999

[22] Filed: Aug. 18, 1987

Related U.S. Application Data

[63] Continuation of Ser. No. 848,353, Apr. 4, 1986, abandoned.

[30] Foreign Application Priority Data

Apr. 18, 1985 [DE] Fed. Rep. of Germany ....... 3513978

[51] Int. Cl.$^4$ ................ C07C 147/14; C07C 149/40; A01N 53/00
[52] U.S. Cl. ..................................... 514/531; 560/124
[58] Field of Search .................. 560/124; 514/531

[56] References Cited

U.S. PATENT DOCUMENTS

| | | | |
|---|---|---|---|
| 4,252,820 | 2/1981 | Lantzsch | 560/124 |
| 4,370,346 | 1/1983 | Punja | 560/124 |
| 4,429,153 | 1/1984 | Punja | 560/124 |

FOREIGN PATENT DOCUMENTS

| | | |
|---|---|---|
| 0031199 | 7/1981 | European Pat. Off. . |
| 0054360 | 6/1982 | European Pat. Off. . |
| 0060617 | 9/1982 | European Pat. Off. . |

*Primary Examiner*—Michael L. Shippen
*Attorney, Agent, or Firm*—Sprung Horn Kramer & Woods

[57] ABSTRACT

Novel insecticidally and acarididally active vinylcyclopropanecarboxylic acid esters of the formula

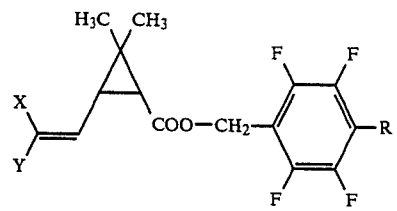

in which
R represents alkylthio, alkylsulphinyl, alkylsulphonyl, amino, monoalkylamino or dialkylamino, and wherein
X and Y either simultaneously represent halogen or
X and Y simultaneously represent alkyl, or in which
X represents $CF_3$,
Y represents Cl and,
R simultaneously represents methylmercapto.

The alcohols of such esters are also new.

7 Claims, No Drawings

VINYLCYCLOPROPANECARBOXYLIC ACID ESTERS

This application is a continuation of application Ser. No. 848,353, filed 4/4/86.

The present invention relates to new vinylcyclopropanecarboxylic acid esters, processes for their preparation and their use as plant protection agents, aginst hygiene pests and pests of stored products, in particular as insecticides and acaricides, and new intermediate products for their preparation and processes for the preparation thereof.

It has already been disclosed that cyclopropanecarboxylic acid esters of similar structure (for example from European Pat. No. A-0,060,617) can be used as insecticides. However, these show a considerably less pronounced activity than the compounds according to the invention.

New vinylcyclopropanecarboxylic acid esters of the formula I

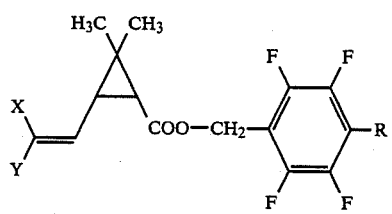

in which

R represents alkylthio, alkylsulphinyl, alkylsulphonyl, amino, monoalkylamino or dialkylamino, and wherein X and Y either simultaneously represent halogen or
X and Y simultaneously represent alkyl, or in which
X represents $CF_3$,
Y represents Cl and,
R simultaneously represents methylmercapto, have been found.

The new vinylcyclopropanecarboxylic acid esters of the formula I

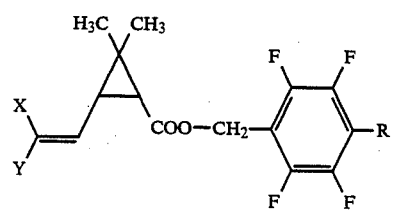

in which

R represents alkylthio, alkylsulphinyl, alkylsulphonyl, amino, monoalkylamino or dialkylamino, and wherein X and Y either simultaneously represent halogen or
X and Y simultaneously represent alkyl, or in which
X represents $CF^3$,
Y represents Cl and,
R simultaneously represents methylmercapto, are obtained by a process in which an acid, or a reactive derivative thereof, of the formula II

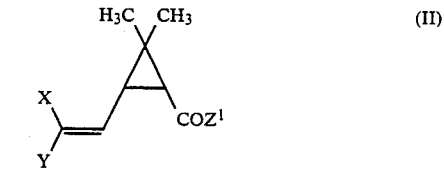

in which

X and Y have the abovementioned meaning and
$Z^1$ denotes halogen, preferably chlorine or OH, is reacted with an alcohol, or a reactive derivative thereof, of the formula III

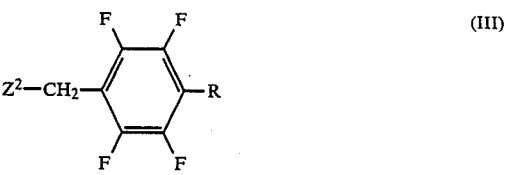

in which

R has the abovementioned meaning and
$Z^2$ represents OH, Cl or Br, if appropriate in the presence of solvents, acid acceptors and/or phase transfer catalysts.

The reaction of the compounds (II) with those of the formula (III) is preferably carried out in the absence of solvents. The new alcohols, and reactive alcohol derivatives, of the formula III

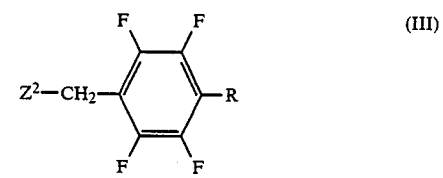

wherein

R and $Z^2$ have the abovementioned meanings, have furthermore been found.

It has furthermore been found that the new alcohols, and alcohol derivatives, of the formula (III) can be prepared by a process in which pentafluorobenzyl alcohol, or its derivatives, of the formula (IV)

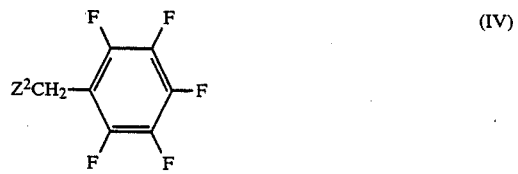

wherein $Z^2$ represents OH, Cl or Br, are reacted with compounds of the formula (V)

wherein

R represents alkylthio, alkylsulphinyl, alkylsulphonyl, amino, monoalkylamino or dialkylamino, if appropriate in the presence of acid acceptors.

In another possibility for the preparation of compounds of the formula (I) in which the radical R represents alkylthio, compounds of the formula

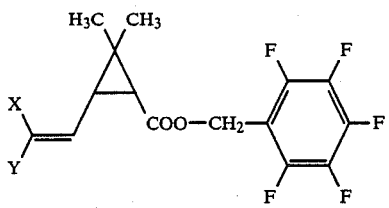
(VI)

in which

X and Y have the abovementioned meaning, are reacted with alkali metal alkylmercaptides (preferably with 1 to 6, in particular 1–4, C atoms), the reaction being carried out only with an alkali metal methylmercaptide if X represents $CF_3$ and Y represents Cl. Preferably, the reaction of pentafluorobenzyl permethrate or pentafluorobenzyl chrysanthemumate with a sodium alkylmercaptide, in particular with sodium methylmercaptide, is carried out in a two-phase system (water/water-immiscible organic solvent, such as, for example, methylene chloride). The reaction is carried out at 0° to 80° C., preferably at room temperature. Another preferred embodiment of this reaction is carried out in the toluene/water/phase transfer catalyst system or also in water-miscible lower alcohols, such as, for example, methanol, ethanol or isopropanol. The organic phase is in each case worked up in a manner which is known per se. The active compounds are preferably separated off by distillation under low pressure. Compounds of type VI are knwon from U.S. Pat. No. 4,183,950.

Surprisingly, the vinylcyclopropanecarboxylic acid esters of the formula (I) according to the invention exhibit a considerably more powerful insecticidal action than the compounds according to European Pat. No. A-0,060,617 known from the prior art.

The compounds occur in 4 stereoisomeric forms, of which the 2 with the absolute configuration R on the C atom carrying the carboxyl group are particularly carriers of the insecticidal action.

Preferred vinylcyclopropanecarboxylic acid esters of the formula (I) according to the invention are those in which R represents alkylthio ($C_1$–$C_6$), alkylsulphinyl ($C_1$–$C_6$), amino, monoalkyl-($C_1$–$C_6$)-amino or dialkyl-($C_1$–$C_6$)-amino and X and Y simultaneously represent chlorine or bromine, or X and Y simultaneously represent alkyl ($C_1$–$C_4$).

Especially preferred vinylcyclopropanecarboxylic acid esters of the formula (I) are those in which R=alkylthio ($C_1$–$C_4$) or alkylsulphinyl ($C_1$–$C_4$) and X and Y=simultaneously chlorine, or X and Y=simultaneously methyl.

If, for example, permethric acid chlordine and 2,3,5,6-tetrafluoro-4-methylmercaptobenzyl alcohol are used as starting components, the course of the reaction can be represented by the following equation:

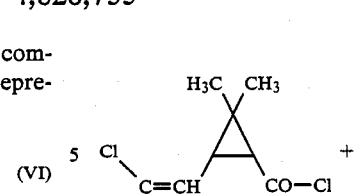

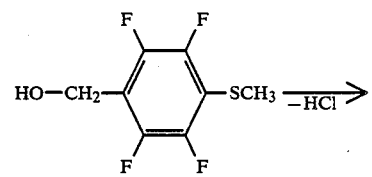

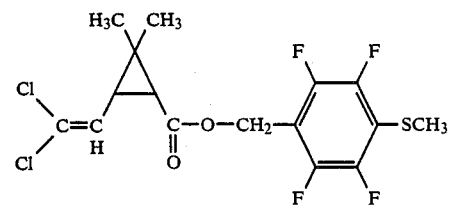

The other preparation variant, reaction of pentafluorobenzyl esters of the formula VI with alkali metal alkylmercaptides, may be illustrated by the following equation:

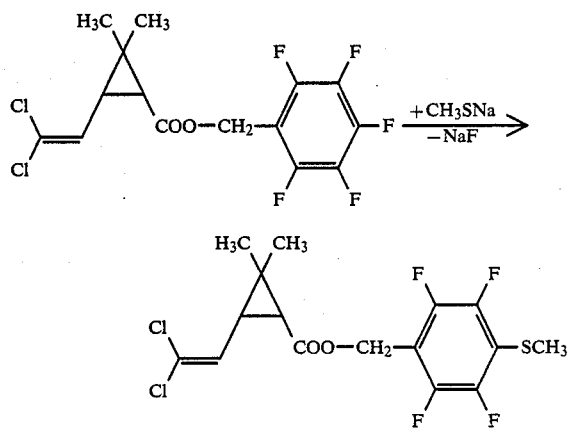

The vinylcyclopropanecarboxylic acids to be used as starting substances and derivatives thereof of the formula (II) are known and can be prepared by generally customary processes described in the literature (compare, for example, DE-OS (German Published Specification) No. 2,326,077, DE-OS (German Published Specification) No. 2,802,962 and U.S. Pat. No. 4,236,026).

Examples which may be mentioned of the compounds of the formula (II) to be used as starting substances are: 3-(2',2'-dichlorovinyl)-2,2-dimethyl-cyclopropanecarboxylic acid (and chloride), 3-(2',2'-dibromovinyl)-2,2-dimethylcyclopropanecarboxylic acid (and chloride), 3-(2',2'-dimethylvinyl)-2,2-dimethyl-cyclopropanecarboxylic acid (and chloride), 1-R-trans-3-(2,2-dichlorovinyl)-2,2-dimethyl-cyclopropanecarboxylic acid (and chloride) and 1-R-cis-3-(2,2-dichlorovinyl)-2,2-dimethyl-cyclopropanecarboxylic acid (and chloride).

The benzyl alcohols to be used as starting substances and reactive derivatives thereof of the formula (III) are new in some cases. The chlorides are preferably employed as reactive derivatives.

Specific examples which may be mentioned of the compounds of the formula III to be used as starting substances are: 4-methylmercapto-2,3,5,6-tetrafluorobenzyl alcohol, 4-propyl-mercapto-2,3,5,6-tetrafluorobenzyl alcohol, 4-ethylmercapto-2,3,5,6-tetrafluorobenzyl alcohol, 4-butylmercapto-2,3,5,6-tetrafluorobenzyl alcohol and 4-dimethylamino-2,3,5,6-tetrafluorobenzyl alcohol.

The reaction of the acids, or reactive derivatives of the acids, of the formula (II) with the alcohols, or the reactive derivatives of the alcohols, (III) is preferably carried out in the absence of solents. In particular, the acid chlorides (formula II, $Z_1$=Cl) are reacted in this manner, the mixture then being warmed until the evolution of hydrogen chloride has ended. It is of course also possible for other acid halides, such as, for example, acid bromides, to be reacted in this manner.

The reaction products are in general worked up by distillation.

To prepare the compounds of the formula I according to the invention by 1. (above) from carboxylic acids or carboxylic acid halides o the formula II and alcohols or chlorides or bromides of the formula III, however, it is also possible for all the customary acid-binding agents, for example, to be used as acid acceptors.

Alkali metal hydroxides, carbonates and alcoholates, such as potassium hydroxide, sodium hydroxide, sodium methylate, potassium carbonate or sodium ethylate, and furthermore aliphatic, aromatic or heterocyclic amines, for example triethylamine, trimethylamine, dimethylaniline, dimethylbenzylamine and pyridine, have proved particularly suitable.

The reaction temperature of the reaction of compounds (II) with compounds (III) can be varied within a substantial range. In general, the reaction of the acid halides with alcohols is carried out between 0° and 100° C., preferably at 15° to 40° C., and the reaction of the carboxylic acid with the halides is carried out between 50° and 150° C., preferably at 80° to 120° C. In the latter case, the reaction is preferably carried out in the presence of a catalyst.

Possible catalysts are all the so-called phase transfer catalysts, such as, for example, crown ethers or quaternary ammonium or phosphonium salts. Quaternary ammonium salts, such as, for example, tetrabutylammonium chloride, tetrabutylammonium bromide, benzltriethylammonium chloride or methyltrioctylammonium chloride, are preferred.

The reaction is in general allowed to proceed under normal pressure. The process for the preparation of the compounds according to the invention is preferably carried out without also using solvents. The reaction can of course also be carried out in the presence of suitable solvents and diluents. Possible solvents and diluents are virtually all the inert organic solvents. These include, in particular, aliphatic and aromatic, optionally chlorinated hydrocarbons, such as benzene, toluene, xylene, benzine, methylene chloride, chloroform, dichloroethane, chlorobenzene or o-dichlorobenzene, or ethers, for example diethyl ether, diisopropyl ether or dibutyl ether, and in addition nitriles, such as acetonitrile and propionitrile.

Another preferred preparation method is the reaction of the alkali metal salts of the acids with corresponding benzyl halides of the formula III ($Z^2$=Cl or Br) in the presence of, for example, catalytic amounts of pentamethylethylenetriamine or similar amines and, for example, in acetonitrile, such as is described, for example, in Synthesis 1975, 805.

The starting components are preferably employed in equimolar amounts for carrying out the process. The reaction components are brought together, if appropriate, in one of the solvents mentioned and the mixture is usually stirred at elevated temperature, after addition of the acid acceptor and, if appropriate, the catalyst, for one or more hours in order to bring the reaction to completion. The reaction mixture is then poured into water and the organic phase is separated off and washed neutral with water. After drying, the solvent is distilled off in vacuo.

The active compounds are well tolerated by plants, have a favorable level of toxicity to warm-blooded animals, and are suitable for combating animal pests, especially insects and arachnida, which are encountered in agriculture, for forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinus, Macrosiphum venae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kueh-* niella, Galleria mellonella, Tineola bisselliella, Tinea pellionella, Hoffmannophila pseudospretella, Cacoecia podana, Capua reticulana, Choristoneura fumiferana, Clysia ambiguella, Homona magnanima and Tortrix viridana. From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium pyslloides, Tribolium spp., Tenebrio molitor, Agriotes spp., Conoderus spp., Melolontha melolontha, Amphimallon solstitialis and Costelytra zealandica. From the order of the Hymenoptera, for example, Diprion spp., Hoplocampa spp., Lasius spp., Monomorium, pharaonis and Vespa spp. From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa. From the order of the Siphonaptera, for example, Xenopsylla cheopis and Ceratophyllus spp. From the order of the Arachnida, for example, Scorpio maurus and Latrodectus mactans. From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The active compounds can be converted to the customary formulations, such as solutions, emulsions, suspensions, powers, foams, pastes, granules, aerosols, natural and synthetic materials impregnated with active compound, very fine capsules in polymeric substances and in coating composition for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl napthalenes, chlorinated aromatics or chloranted aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

it is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention are used in the form of their commercially available formulations and/or the use forms prepared from these formulations.

The active compound content of the use forms prepared from the commercially available formulations can vary within wide limits. The active compound concentration of the use forms can be from 0.0000001 to 100% by weight of active compound, preferably between 0.01 and 10% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

EXAMPLE A

Test insects: Blatta orientalis ♀ ♀

Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m² of filterpaper varies, depending on the concentration of the active compound solution. About 5 test insects are then introduced into the Petri dish, and the dish is covered with a glass lid.

The condition of the test insects is checked 3 days after the experiments have been set up. The destruction in % is determined.

In this test, for example, the following compounds of the preparation examples shown a superior activity compared with the prior art: 1, 2, 3, 4, 7 and 10.

EXAMPLE B

LT$_{100}$ test for Diptera
Test insects: *Aedes aegypti*
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m² of filterpaper varies, depending on the concentration of the active compound solution. About 25 test insects are then introduced into the Petri dish, and the dish is covered with a glass lid.

The condition of the test insects is checked continuously. The time required for a 100% knock-down effect is determined.

In this test, for example, the following compounds of the preparation examples show a superior activity compared with the prior art: 1, 2, and 4.

EXAMPLE C

Laphygma test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specific periods of time, the destruction in % is determined. 100% means that all the caterpillars have been killed; 0% means that none of the caterpillars have been killed.

In this test, for example, the following compounds of the preparation examples show a superior activity compared with the prior art: 1, 2, 3 and 4.

EXAMPLE D

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (oryza sativa) are treated by being dipped into the preparation of active compound of the desired concentration and are infested with the green rice cicada (*Nephotettix cincticeps*) while the seedlings are still moist.

After the specified periods of time, the destruction in % is determined. 400% means that all the cicadas have been killed, 0% means that none of the cicadas have been killed.

In this test, for example, the following compounds of the preparation examples show a superior activity compared with the prior art: 1, 2, 4, and 19.

EXAMPLE E

Test insect: *Phorbia antiqua* grubs (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is acced and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds of the preparation examples show a superior activity compared with the prior art: 1, 2, 3, 4, 7 and 10.

EXAMPLE F

Test insect: *Diabrotica balteata*—larvae in the soil
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practially no importance, only the amount by weight of active compound per unit volume of soil, which is given in ppm (=mg/l) being decisive. The soil is filled into 0.5 l pots and the pots are left to stand at 20° C.

Immediately after being set up, 6 pregerminated corn seeds are placed in each pot. After 2 days, the corresponding test insects are placed in the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds of the preparation examples show a superior activity compared with the prior art: 1, 2, 3, 4, 7 and 10.

EXAMPLE G $LT_{100}$ test for Diptera

Test insects: *Musca domestica*

Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per $m^2$ of filterpaper varies, depending on the concentration of the active compound solution. About 25 test insects are then introduced into the Petri dish, and the dish is covered with a glass lid.

The condition of the test insects is checked continuously. The time required for a 100% knock-down effect is determined.

In this test, for example, the following compounds of the preperation example show a superior activity compared with the prior art: 1, 2, 4 and 19.

EXAMPLE 1

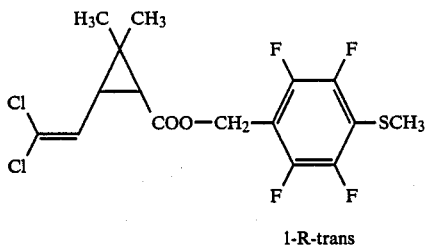

1-R-trans 0.1 mole (20.3 g) of 1 R trans-permethric acid chloride and 0.1 mole (22.7 g) of 2,3,5,6-tetrafluoro-4-methylmercaptobenzyl alcohol were warmed together at 50° to 70° C., without a solvent, until the evolution of hydrogen chloride has ended. The product was then distilled in vacuo. 39 g of the optically active 1R trans compound of the above formula were obtained (melting point: 53°–54° C.; IR spectrum: 3040, 2960, 2940, 2880, 1730, 1635, 1615, 1470, 1425, 1395, 1385, 1345, 1280, 1230, 1150–1180, 1115, 1050, 990, 970, 930, 910, 885, 860 and 780.

The following compounds were prepared in an analogous manner: General formula:

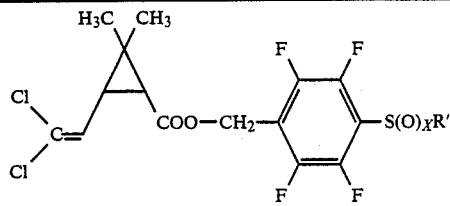

| Example No. | R' | X | Stereochemistry | Physical data |
|---|---|---|---|---|
| 2 | $CH_3$ | 0 | racemic cis/trans | Boiling point 0.1:145° C. |
| 3 | $CH_3$ | 0 | optically active 1R cis | Melting point: 52° C. |
| 4 | $CH_3$ | 0 | optically active 1R cis/1R trans | Boiling point 0.1:145° C. |
| 5 | $C_2H_5$ | 0 | optically active 1R trans | Melting point: 87° C. |
| 6 | $nC_4H_9$ | 0 | optically active 1R trans | Boiling point 0.1:165° C. |
| 7 | $CH_3$ | 1 | racemic cis/trans | |
| 8 | $C_2H_5$ | 1 | | |
| 9 | $CH_3$ | 2 | | |

EXAMPLE 10

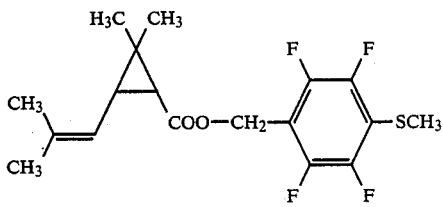

37 g of the (±) cis/trans mixture of the above compound were obtained in an analogous manner to Example 1 using 0.1 mole of (±) cis/trans chrysanthemic acid chloride and 0.1 mole of 2,3,5,6-tetrafluoro-4-methyl-mercaptobenzyl alcohol.

IR data: 2930–3000, 2880, 1730, 1640, 1470, 1425, 1380, 1360, 1325, 1275, 1240, 1200, 1110–1170, 1050, 1020, 990, 930, 910, 855 and 780.

The following compounds can be prepared in an analogous manner to Example 10: general formula:

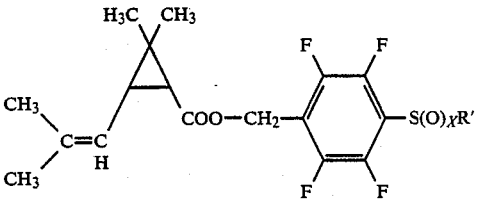

| Example No. | X | R'' | Stereochemistry |
|---|---|---|---|
| 11 | 0 | $CH_3$ | (±) cis/trans |
| 12 | 0 | $CH_3$ | optically active 1R cis |
| 13 | 0 | $CH_3$ | optically active 1R trans |
| 14 | 0 | $C_2H_5$ | optically active 1R trans |
| 15 | 0 | $nC_4H_9$ | optically active 1R trans |
| 16 | 1 | $CH_3$ | |
| 17 | 1 | $C_2H_5$ | |
| 18 | 2 | $CH_3$ | |

EXAMPLE 19

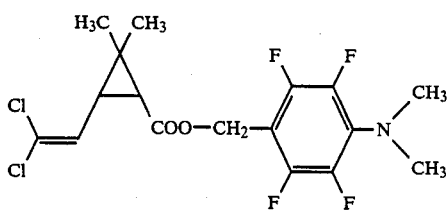

0.1 mole (20.3 g) of 1R-trans-permethric acid chloride and 0.1 mole (22.3 g) of 2,3,5,6-tetrafluoro-4-dimethylaminobenzyl alcohol were reacted analogously to Example 1.

29 g of the 1R-trans isomer of the abovementioned compound were obtained (oil). IR data: 2860–3000, 2820, 1730, 1650, 1515, 1490, 1440, 1430, 1385, 1345, 1280, 1260, 1230, 1170, 1100, 1050, 1000, 925, 895, 780 and 750.

EXAMPLE 20

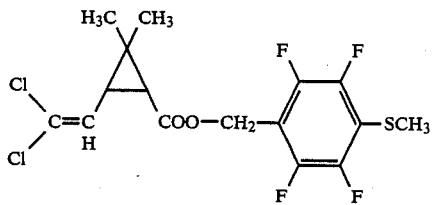

0.1 mole (26 g) of the potassium salt of permethric acid were brought together with 0.1 mole (24 g) of 2,3,5,6-tetrafluoro-4-methylmercaptobenzyl chloride and 0.005 mole (0.8 g) of pentamethyldiethylenetriamine in 100 ml of acetonitrile. The mixture is heated under reflux, with stirring, until the 2,3,5,6-tetrafluoro-4-methylmercaptobenzyl chloride has been consumed, and is concentrated and the residue is extracted by shaking with water/hexane. The organic solution is concentrated and the residue is then distilled under a high vacuum.

Melting point: 54° C.

The compounds of Examples 2 to 19can be reacted in an analogous manner to Example 20 to give the corresponding pyrethroid end products.

EXAMPLE 20a

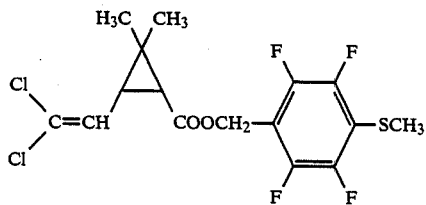

0.1 mole of pentafluorobenzyl (±) cis/trans permethrate in 150 ml of methylene chloride was added dropwise to a solution of 0.1 mole of sodium methylmercaptide in 100 ml of water at 20° C. under nitrogen. When the reaction becomes neutral, the organic phase is concentrated. After distillation using a bulb tube (oven temperature of 230° C., 0.05 mm), the title compound, which, according to the NMR spectrum, is pure, is obtained in a yield of 96 percent. Melting point: 53°–54° C.

The tetrafluoro-4-methyl-mercaptobenzyl 1 R trans permethrate is obtained in the same manner from pentafluorobenzyl 1 R trans-permethrate. Melting point 53°–54° C.

The abovementioned reaction can also be carried out in the system toluene/water/phase transfer catalyst or, for example, in lower alcohols, such as methanol, ethanol or isopropanol. The starting material pentafluorobenzyl (±) cis/trans permethrate is known from U.S. Pat. No. 4,183,950.

EXAMPLE 21

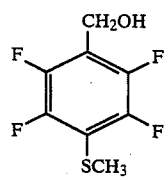

100 ml of isopropanol are taken at 0° C. in a 250 ml three-necked stirred flask apparatus with a thermometer, condenser and cooling bath, 5 g of methylmercaptan are then passed in 4 g of powdered sodium hydroxide are added. Thereafter, 20 g of pentafluorobenzyl alcohol are added dropwise at 0° C., via a dropping funnel which can be heated, in the course of 15 minutes. The mixture is then warmed slowly to the reflux temperature (83°–84° C.) and stirred at this temperature for one hour. The mixture is cooled and poured onto ice-water. The greasy crystals formed are taken up in methylene chloride.

The two phases are then separated and the organic phase is dried over sodium sulphate and distilled on a column. 16.6 g of 2,3,5-tetrafluoro-4-methylmercaptobenzyl alcohol are obtained (boiling point 16 mbar: 145°–146° C.).

It is understood that the specification and examples are illustrative but not limitative of the present invention and that other embodiments within the spirit and scope of the invention will suggest themselves to those skilled in the art.

We claim:

1. A vinylcyclopropanecarboxylic acid ester of the formula

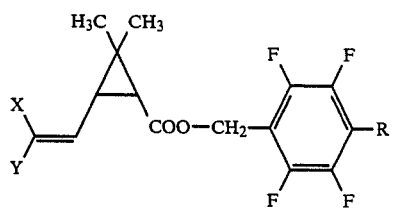

in which

R is methylthio or methylsulphinyl, and

X and Y each is halogen.

2. A compound according to claim 1, wherein such compound is 2,3,5,6-tetrafluoro-4-methylmercaptobenzyl permethrate of the formula

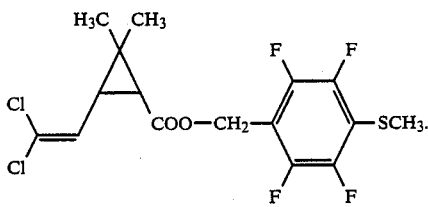

3. A compound according to claim 1, wherein such compound is 2,3,5,6-tetrafluoro-4-methylmercaptobenzyl permethrate of the formula

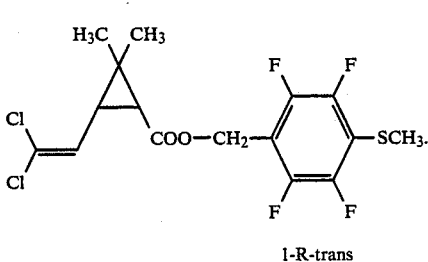

1-R-trans

4. A compound according to claim 1, wherein such compound is 2,3,5,6-tetrafluoro-4-methylsulphinylbenzyl permethrate of the formula

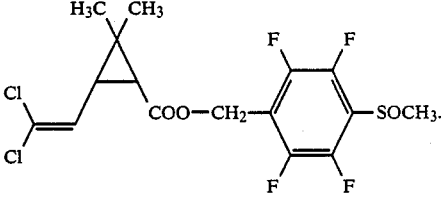

1-R-trans

5. An insecticidal and acaricidal composition comprising an insecticidally or acaricidally effective amount of a compound according to claim 1 and a diluent.

6. A method of combatting insects or acarids which comprises applying to such insects, acarids or a habitat thereof an insecticidally or acaricidally effective amount of a compound according to claim 1.

7. The method according to claim 5, wherein such compound is
2,3,5,6-tetrafluoro-2-methylmercaptobenzyl permethrate, or
2,3,5,6-tetrafluoro-4-methylsulphinylbenzyl permethrate.

* * * * *